United States Patent [19]

Hori et al.

[11] 4,028,106

[45] June 7, 1977

[54] METHOD FOR DEVELOPING AN EXPOSED SILVER HALIDE COLOR PHOTOSENSITIVE MATERIAL

[75] Inventors: Haruo Hori; Shoji Kikuchi; Hajime Wada; Sadatosi Kobayasi; Takaya Endo, all of Hino, Japan

[73] Assignee: Konishiroku Photo Industry Co., Ltd., Tokyo, Japan

[22] Filed: Nov. 4, 1975

[21] Appl. No.: 628,762

[30] Foreign Application Priority Data

Nov. 5, 1974 Japan .............................. 49-127314

[52] U.S. Cl. ........................................ 96/55; 96/100
[51] Int. Cl.² ...................... G03C 7/00; G03C 1/40
[58] Field of Search ...................... 96/100, 56.5, 55

[56] References Cited

UNITED STATES PATENTS

| | | | |
|---|---|---|---|
| 3,419,390 | 12/1968 | Cressman et al. | 96/100 |
| 3,489,759 | 1/1970 | Fields et al. | 96/56.5 |
| 3,930,866 | 1/1976 | Oishi et al. | 96/100 |
| 3,933,500 | 1/1976 | Shiba et al. | 96/56.5 |

Primary Examiner—Mary F. Kelley
Attorney, Agent, or Firm—Bierman & Bierman

[57] ABSTRACT

An improved method for developing an exposed silver halide color photosensitive material is disclosed which comprises conducting the development in the presence of a cyan coupler. The coupler has, in the active position thereof, the following split-off group:

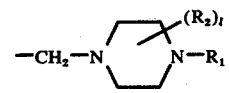

wherein $R_1$ is an aliphatic hydrocarbon residue, an aromatic hydrocarbon residue, or a heterocyclic ring residue; $R_2$ is an aliphatic hydrocarbon residue or an aromatic hydrocarbon residue; $l$ is an integer of 0 to 4 inclusive.

7 Claims, No Drawings

METHOD FOR DEVELOPING AN EXPOSED SILVER HALIDE COLOR PHOTOSENSITIVE MATERIAL

DETAILED DESCRIPTION OF THE INVENTION

This invention relates to a novel coupler for use in photography. More particularly, the invention relates to a novel coupler for use in photographic process using silver halide as a photosensitive component.

In photography, silver halides are conventionally used for recording light information because they possess excellent photographic characteristics such as sensitivity and gradation. In order to obtain a colored image, the silver halide is generally combined with a certain kind of color-forming compound which is reacted with a certain kind of a reactive compound to form a dye corresponding to the information recorded on the silver halide. This results in the formation of a dye image. This color-forming compound is generally called a coupler, and the reactive compound is a color-forming developing agent such as an aromatic primary amine developing agent.

As is well known in the art, when light is recorded imagewise on sliver halide having a development center and the silver halide is developed in the presence of a coupler with a developing agent, the developing agent reduces the silver halide to reduced silver. The developing agent per se is oxidized to form an active oxidation product of the developing agent and this oxidation product reacts with the coupler to form a dye. This process results in the formation of a dye image corresponding to the information recorded on the silver halide.

The reaction between the coupler and developing agent is performed at the active position of the coupler, and the active position resides generally at an active methine or methylene group in the molecule of the coupler.

A coupler having a hydrogen atom at this active position is called a 4-equivalent coupler. If a coupler has, at this active position, a group which will easily split during the reaction between the coupler and developing agent; namely, a so called split-off group, it is referred to as a 2-equivalent coupler.

In the reaction of a 4-equivalent coupler with a developing agent, 4-equivalents of silver halide having a development center are required per active position. In the case of a 2-equivalent coupler, only 2-equivalents of a silver halide are required. Therefore, the 2-equivalent coupler provides a dye image having a higher concentration than the 4-equivalent coupler, based on equal amounts of developed silver. Further, in the case of the 2-equivalent coupler, if a bonding part of the split-off group (bonding group) is appropriately chosen, it is possible to impart a development-inhibiting activity to a compound formed by splitting of the split-off group. For example, a 2-equivalent coupler having a split-off group with a thio group (-s-) as the bonding group is called a development inhibitor-releasing coupler (D. I. R. coupler). Since this coupler inhibits development in proportion to the amount of developed silver, it can be utilized in various ways. For example, this D. I. R. coupler exhibits a so called intra-image effect in its own layer, such as controlling the image tone and finely dividing the image particles. Additonally, the D.I.R. coupler exhibits an inter-image effect on other layers, such as improving the dye hue.

Further, the coupler of this type has various effects on other layers. By virtue of these effects, the coupler of this type is also utilized in diffusion transfer type photography.

Some 2-equivalent type couplers, for instance, those in which a dye component is included in the split-off group can be used in the diffusion transfer type photography, in this case, the split dye is utilized for the formation of a diffused dye image on an image-receiving layer. A coupler of this type is called a diffusible dye-releasing coupler (D. D. R. coupler). Further, some colored 2-equivalent couplers have a masking effect which results in correcting the color of the dye image. A coupler of this type is called a colored coupler.

Because of the foregoing substantial advantages over 4-equivalent couplers 2-equivalent couplers tend to be used more frequently than 4-equivalent couplers.

Although known 2-equivalent couplers are advantageous over 4-equivalent couplers in various characteristics, they are still insufficient in the dye-forming rate and are likely to cause fog or contamination in a silver halide-containing photosensitive layer. They are also defective in that they cannot be dispersed in a photosensitive layer at a sufficient dispersion concentration. Elimination of these defects in 2-equivalent type couplers has been sought in the art.

It is a primary object of this invention to provide a novel 2-equivalent type coupler in which the foregoing defects involved in conventional 2-equivalent type couplers are overcome.

Another object of this invention is to provide a 2-equivalent type coupler having excellent photographic characteristics.

Still another object of this invention is to provide a silver halide photosensitive material containing the nanel 2-equivalent type coupler and a photograhic process for using it.

This invention more specifically relates to a 2 equivalent photographic cyan coupler having, on the active position thereof, a split-off group represented by the following formula [I]:

Formula [1]

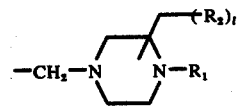

wherein $R_1$ is an aliphatic hydrocarbon residue, an aromatic hydrocarbon residue, or a heterocyclic ring; $R_2$ is an aliphatic hydrocarbon residue or an aromatic hydrocarbon residue; and $l$ is an integer of 0 to 4 inclusive.

The above 2-equivalent type coupler of this invention has a piperidinomethyl bonding group which results in the coupler having high dye formation speed and no fog, color contamination, etc. in its photosensitive layers. Additionally, the present coupler is more effectively dispersed at a high concentration in layers such as photosensitive layers of photographic elements.

In addition, dyes derived from this coupler are excellent in stability against heat, humidity and light as well as in light absorption characteristics. These dyes show no absorption of unnecessary light and good absorption of necessary light. Moreover, the coupler does not restrain development which is characteristic of certain known 2 equivalent couplers.

For instance, silver halide photograhic light sensitive materials, containing 2 equivalent couplers of this invention, can be thinner and improved in color, resolution power and sharpness.

Furthermore, since they are improved in transparency for layers under a layer containing the couplers, sensitivity is improved in a multi-layer light sensitive materials: Typical instances of 2 equivalent couplers of this invention are represented by the following formula [II] or [III]:

Formula [II]

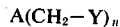

Formula [III]

wherein A and A' are respectively a n-equivalent residue and a mono-equivalent residue of a cyan coupler; Y is monovalent and N-substituted piperazinyl; Y' is m-equivalent organic group having piperazinyl directly attaching to the A'—CH$_2$— group; and n and m are individually a positive integer.

The above general formulas [II] and [III] are of a basic type and the mixture thereof can be used effectively in this invention.

As mentioned above, since the cyan coupler residue is that not having a hydrogen atom or a split-off group on the active position and where the coupler has more than two active positions in one molecule, each of the split off groups introduced to the active positions may be the same or different. In this case, the coupler includes hydrogen or hydrogen atoms at the active positions. Preferably all the active positions are filled by the split-off group of this invention. In the above formulas, Y and Y' can individually be piperazinyl having such a substituent or substituents as defined in R$_1$ in formula [I]

Typical examples of the aliphatic hydrocarbon residue set forth in the formulas are substituted or unsubstituted alkyl, acyl, formyl, amino carbonyl, etc. As alkyl, there can be mentioned methyl, ethyl, butyl, benzyl and the like. As acyl, there can be mentioned acetyl, benzoyl, phenoxyacetyl and the like.

Typical instances of the aromatic hydrocarbon residue are aryl, more specifically substituted or unsubstituted phenyl, naphthyl and the like. Substituted or unsubstituted pyridyl, quinolyl and the like are for typical instances of the heterocyclic ring.

As Y' as defined in the formulas, in addition to two equivalent piperazinyl groups directly attached to two A'—CH$_2$—groups (wherein A' is as defined before), a m-equivalent group can be used which includes more than two piperazinyl groups directly attached to a A'—CH$_2$— group and which can further comprise other organic groups between the more than two piperazinyl groups. For example, there can be mentioned two equivalent complex groups such as two piperazinyls having a two equivalent aliphatic hydrocarbon residue there between at the carbon or nitrogen position of the piperazine ring, or having both two equivalent aliphatic hydrocarbon residues and arylene therebetween as in the above. These two equivalent aliphatic hydrocarbon residues and arylene are included in the form of a combined two equivalent group which may be combined, as either being brocks or at ramdom, using the certain member ($k$) of two èquivalent aliphatic hydrocarbon residues and the certain member ($l$) of arylenes wherein $k$ and $l$ are individually positive integer. Preferably, $n$ and $m$ are individually 1 or 2. However, in case a body structure is of a cyan coupler known as being a polymer coupler, for instances, $n$ and $m$ can be more than 3.

Representative examples of coupler residues as a cyan coupler residue are represented by the following general formula [IV] [V] and [VI]

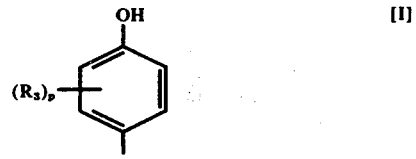

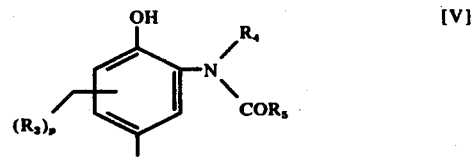

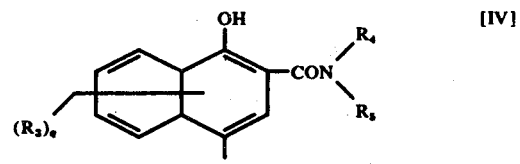

wherein R$_3$ stands for a hydrogen or halogen atom, an aliphatic hydrocarbon residue or a group —O—R$_6$ or —S—R$_6$ in which R$_6$ is an aliphatic hydrocarbon residue, and when a plurality of groups R$_3$ are present in one molecule, they can be the same or different and further the hydrocarbon residue can have a substituent; R$_4$ and R$_5$ stand for a member selected from aliphatic or aromatic hydrocarbon residues, and heterocyclic-ring residues of one of them can be a hydrogen atom, these groups can have a substituent, and R$_4$ and R$_5$ together can form a nitrogen-containing heterocyclic-ring; $p$ is an integer of 1 to 3; and $q$ is an integer of 1 to 5.

In the foregoing formulas, the aliphatic hydrocarbon residue can be either saturated or unsaturated, and it can be straight, branched or cyclic. Preferred examples of the aliphatic hydrocarbon residue include alkyl groups such as methyl, ethyl, isobutyl, dodecyl, octadecyl, cyclobutyl and cyclohexyl, and alkenyl groups such as allyl. Typical examples of the aryl group are phenyl and naphthyl, and typical examples of the hetero-ring residue are pyridyl, quinolyl, thienyl, piperidyl and imidazolyl. The sustituent introduced into such aliphatic, aryl or heterocyclic-ring residue, can be halogen, nitro, hydroxyl, carboxyl, amino, a substituted amino group, a sulfo group, and substituted and unsubstituted alkyl, alkenyl, aryl, heterocyclic-ring, alkoxy, aryloxy, arylthio, arylazo, acylamino, carbamoyl, ester, acyl, acyloxy, sulfoneamide, sulfamoyl, sulfonyl, morpholino, piperazyl and imidazolyl. As the heterocyclic-ring formed by R$_4$ and R$_5$, there can be peferably used the above-exemplified nitrogen-containing hetero-rings. In the above formulas [II] and [III], the aliphatic hydrocarbon residue includes both saturated and unsaturated one in the form of a chain, a branched chain or a ring. Examples of a monovalent group are alkyl, alkenyl and the like, more specifically methyl, ethyl, iso-butyl, octyl, tertial octyl, octadecyl, cyclobutyl, cyclohexyl, 2-norbonyl and the like. As a 2 equivalent group, preferred examples are methylene, ethylene, butylene, hexylene and the like. Typical examples of the aromatic hydrocarbon residue are aryl and arylene, preferably phenyl, naphthyl, phenylene, naphthylene and the like. Preferred examples of the heterocyclic ring are 5 to 6 membered heterocyclic residues comprising a hetero atom or atoms such as nitrogen, sulfur and, oxygen. For example, thienyl, pyridinyl, quinolyl, oxyadiazolyl as a monovalent group and quinolyene as a two equivalent group. As the acyl group, there can be mentioned acetyl, benzoyl, naphthoyl, and as thioacyl, preferably thio acetyl, thiobenzoyl, thionaphthoyl and the like. As examples of sulfonyl, there can be mentioned phenylsulfonyl, chlorosulfonyl and methanesulfonyl.

Preferred examples of the split-off group other than Cp in the above general formula [I] are illustrated below.

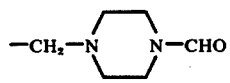

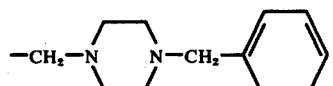

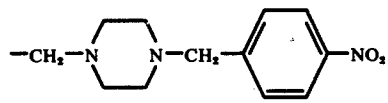

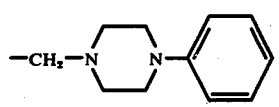

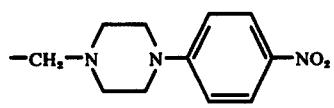

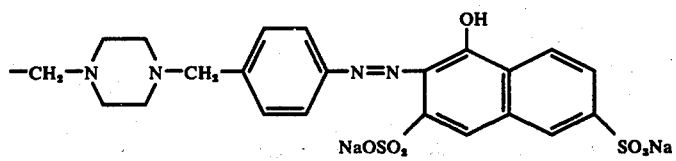

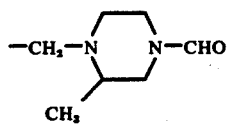

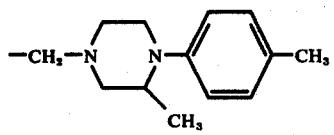

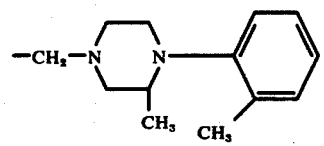

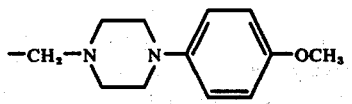

-continued
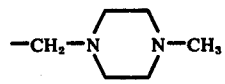
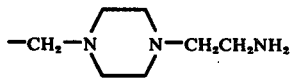
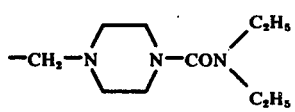
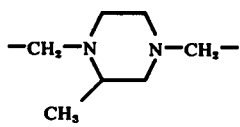
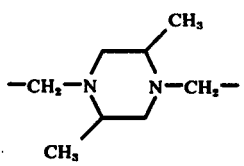
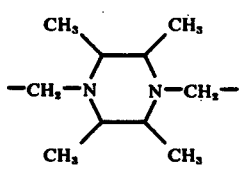
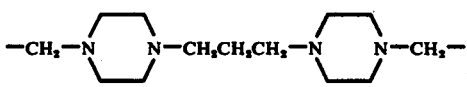
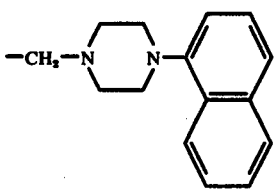
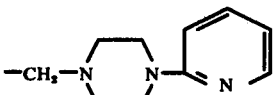
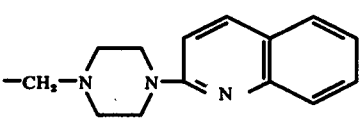
According to this invention, couplers, as set forth in formulas [IV], [V] and [VI], having the bove split-off groups at the active positions have many advantages. For example they are excellent as photograhic couplers as previously indicated. This is due to the bonding groups.

The couplers according to this invention are exemplified hereinafter but the scope of this invention is not limited by the examples.
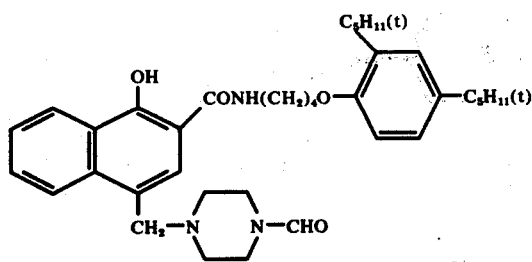
(1)
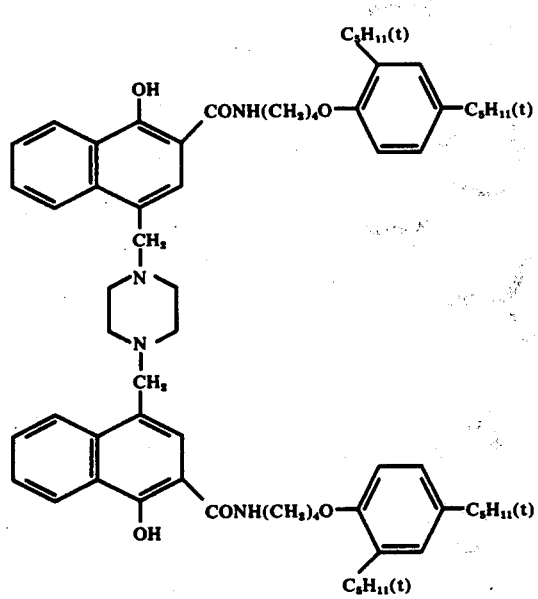
(2)
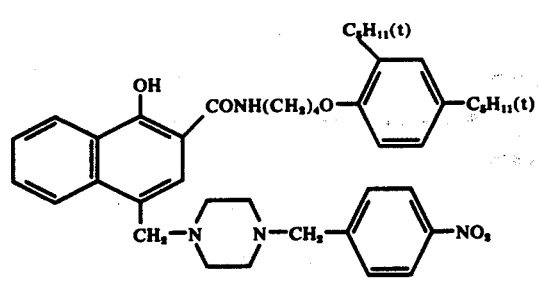
(3)
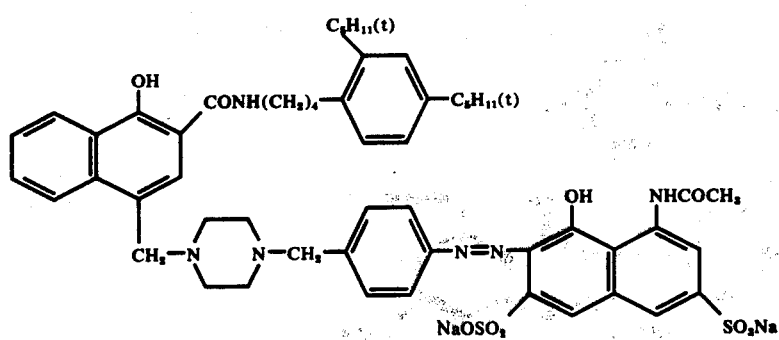
(4)

-continued
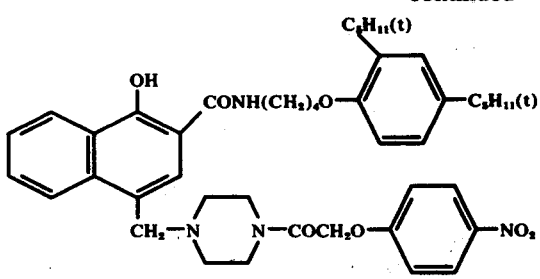
(5)
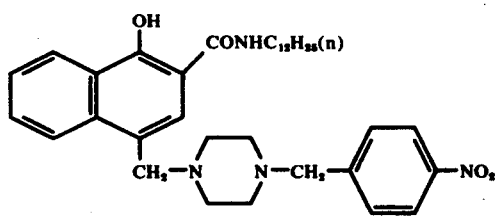
(6)
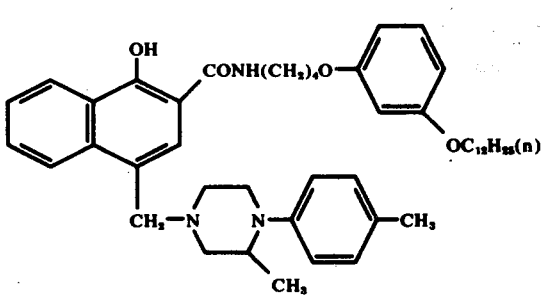
(7)
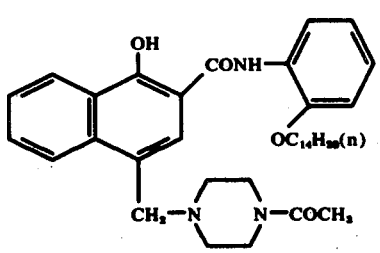
(8)
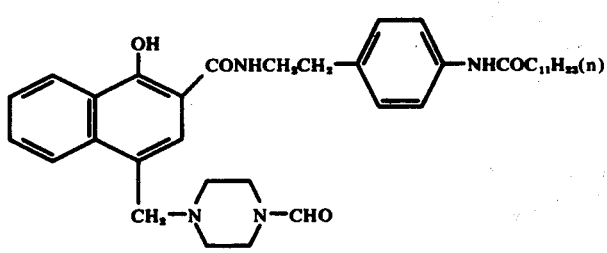
(9)
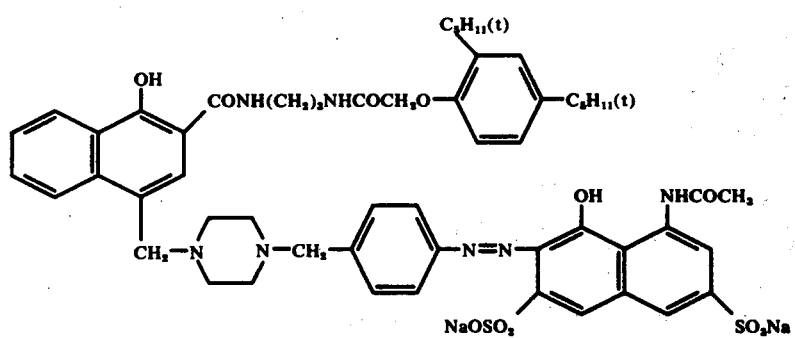
(10)

-continued
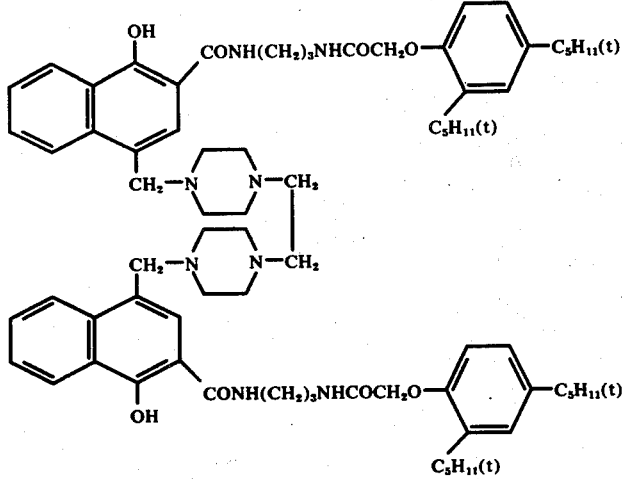
(11)
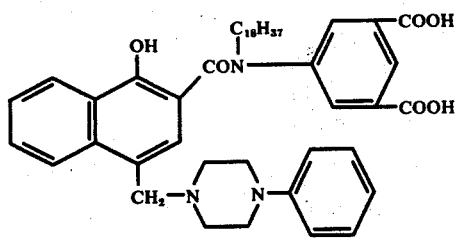
(12)
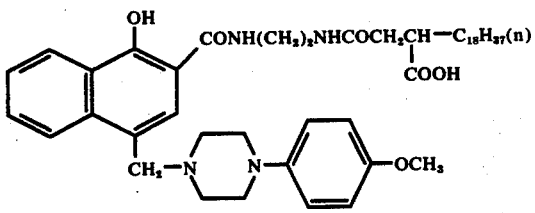
(13)
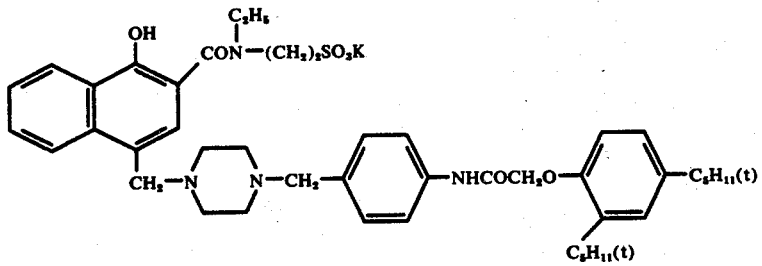
(14)
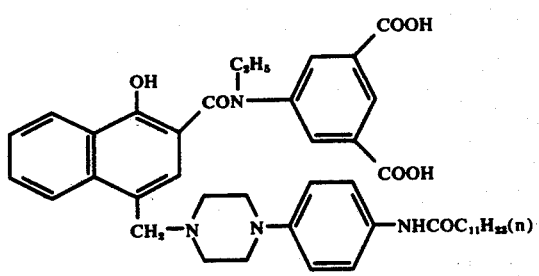
(15)
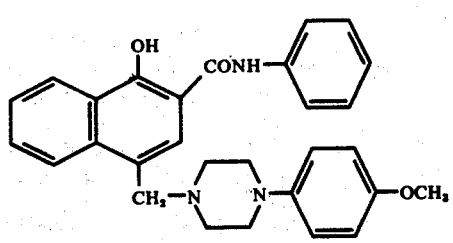
(16)

(17)
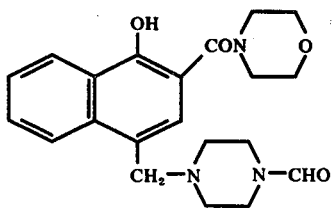

(18)
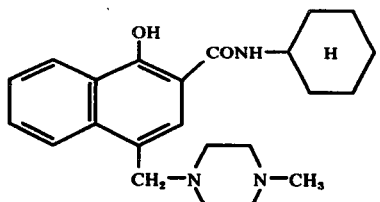

(19)
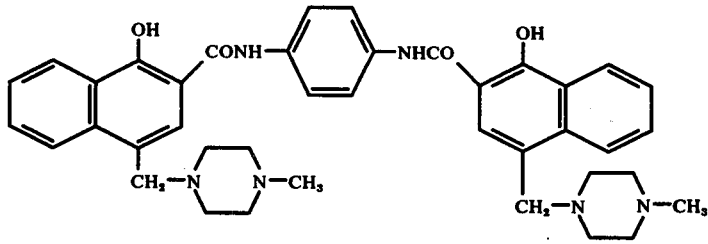

(20)
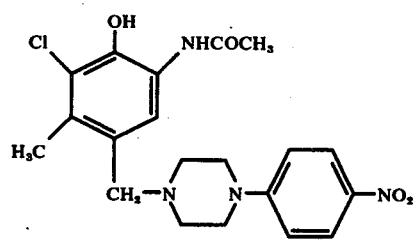

(21)
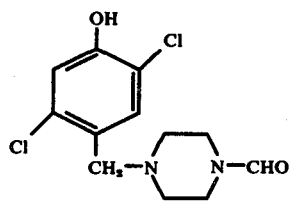

(22)
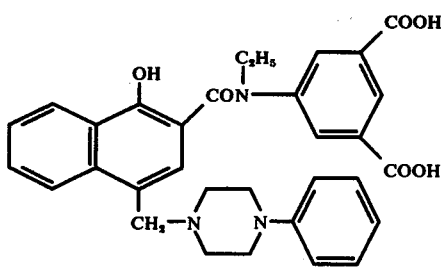

Cyan couplers having piperazinyl according to this invention can generally be synthesized by the following method:

a naphthol type can cyan coupler such as 1-hydroxy-2-naphtho anilido, 1-hydroxy-2-{N-[4-(2,4-di-t-pentyl phenoxy)butyl]}naphthoamido, and 1-hydroxy-2-[N(2-n-tetradecyloxyphenyl]naphthoamido or a phenyl type cyan coupler such as 6-chloro-5-methyl-2-acetoamido phenol, and 2,5-di-chlorophenol is stirred, in a solution of dioxane, methanol or the like, in the presence of 37% formalin and substituted or unsubstituted piperazine, such as N-formyl piperazine, N-benzylpiperazine, and piperazine at a room temperature or more for an appropriate period of time. After the completion of the reaction, the solvent is removed and the residue is then recrystalized from an appropriate solvent such as benzene and ethanol in order to obtain the desired coupler.

Examples of the synthesis of the coupler according to this invention are illustrated below.

SYNTHESIS EXAMPLE 1

0.01 mole of 1-hydroxy-2-{N-[4-(2,4-di-t-pentyl-phenoxy) butyl]}naphthoamido was dissolved in 30 ml of dioxane to obtain a solution 0.01 mole of N-formyl-piperazine was added dropwise into 0.011 mole of 37% formalin under stirring for fifteen minutes at a room temperature. The resulting product was then placed into the above solution and stirred for three hours at 40° – 45° C in order to complete the reaction. The solvent was removed under reduced pressure. The residue was recrystalized from ethanol. The obtained residue had a melting point of 151 to 152° C and a 41% yield. The elementary analysis of this compound (1) is set forth below.

SYNTHESIS EXAMPLE 2

0.01 mole of 1-hydroxy-2-{N-[4(2,4-di-t-pentyl phenoxy) butyl]}naphthoamido was dissolved in 30 ml of dioxane to obtain a solution. 0.01 mole of N-(4-nitrobenzil) piperazine and 0.01 mole of N-(4-nitrobenzil) piperazine (dissolved in ethanol) for were mixed 15 minutes. This resulting product was placed into the above solution for 5 hours at 60° C to complete the reaction. The solvent was removed under reduced pressure. The residue was recrystalized from the mixture of benzene and petroleum benzine, so that a compound having a melting point of 158° to 159° C was obtained. The result of elementary analysis of this compound (3) is set forth below.

SYNTHESIS EXAMPLE 3

Compound 3 obtained according synthesis example 2 was conventionally reduced by zinc and hydrochloride to get an amino compound and then diazotized. The resulting compound was reacted, by coupling reaction, with 8-acetoamido-3,6-di-sulfo-α-naphthol disodium salt to obtain a compound having a melting point of more than 300° C. The yield was 56%. The result of elementary analysis of this compound (4) is set forth below.

SYNTHESIS EXAMPLE 4

0.085 mole of compound 1 was stirred in 45 ml of 30% hydrochloride and 45 ml of water for two hours at 80° to 90° C. 0.017 mole of the thus obtained 1-hydroxy-4-piperadinomethyl-2-{N-[4-(2,4-di-t-pentyl-phenoxy)butyl]}naphthoamido was dissolved in a mixed solvent of 200 ml of benzene and 100 ml of dioxane. Then, 2 ml of triethylamine was added thereto to obtain a solution 0.02 mole of 4-nitrophenoxyacetyl-chloride (melting point: 84° to 85° C) was added to a mixture of 100 ml of benzene and 10 ml of dioxane. The resulting product was placed into the above solution for 30 minutes and then stirred for 2 hours at room temperature and for 5 hours at 50° C. The solvent was then removed under reduced pressure. The residue was recrystalized from the mixture of benzene and petroleum benzine to obtain a compound (melting point: 178° to 179° C) and a yield of 65%. The result of the elementary analysis of this compound (5) is set forth below.

The other couplers were similarly synthesized according to the above procedure. The results of the elementary analysis for the so-obtained couplers are shown in the following table.

| Compound | elementary analysis | | | | | |
|---|---|---|---|---|---|---|
| | Calculated value (%) | | | Measured value (%) | | |
| | C | H | N | C | H | N |
| 1 | 73.38 | 8.54 | 6.98 | 73.62 | 8.44 | 6.83 |
| 2 | 76.94 | 8.74 | 5.28 | 77.10 | 8.51 | 5.05 |
| 3 | 72.85 | 7.96 | 7.90 | 72.62 | 7.73 | 7.65 |
| 4 | 60.31 | 5.89 | 7.67 | 60.95 | 6.18 | 7.36 |
| 5 | 70.19 | 7.50 | 7.44 | 70.32 | 7.75 | 7.22 |
| 6 | 71.40 | 8.22 | 9.52 | 71.10 | 8.32 | 9.73 |
| 7 | 76.52 | 8.80 | 5.82 | 76.33 | 8.97 | 5.98 |
| 8 | 75.34 | 71.55 | 6.94 | 75.55 | 71.42 | 6.72 |
| 9 | 72.28 | 8.20 | 9.11 | 71.95 | 8.35 | 9.29 |
| 10 | 59.09 | 5.76 | 8.61 | 58.31 | 5.44 | 8.32 |
| 11 | 73.27 | 8.26 | 7.32 | 73.51 | 8.37 | 7.57 |
| 12 | 74.10 | 8.16 | 5.40 | 73.87 | 8.02 | 5.12 |
| 13 | 71.72 | 8.96 | 7.12 | 71.42 | 8.76 | 7.32 |
| 14 | 65.66 | 7.22 | 6.80 | 65.02 | 7.50 | 6.47 |
| 15 | 70.38 | 7.25 | 7.46 | 70.30 | 7.40 | 7.13 |
| 16 | 77.13 | 6.47 | 9.30 | 76.87 | 6.21 | 9.17 |
| 17 | 65.78 | 6.57 | 10.96 | 65.65 | 6.28 | 10.70 |
| 18 | 72.41 | 8.19 | 11.01 | 72.65 | 8.02 | 11.28 |
| 19 | 71.40 | 6.59 | 12.49 | 71.21 | 6.80 | 12.71 |
| 20 | 57.35 | 5.53 | 13.38 | 57.10 | 5.31 | 13.64 |
| 21 | 49.84 | 4.88 | 9.69 | 49.60 | 4.96 | 9.47 |
| 22 | 69.42 | 5.64 | 7.59 | 69.31 | 5.76 | 7.79 |

The so obtained couplers of this invention are characterized by a high dye-forming speed and, they exhibit, as mentioned above, a much higher dye-forming speed in color development than conventional 4-equivalent type cyan couplers. Further, their dye-forming speed is higher than that of a 2-equivalent type coupler having, as a split-off group, aryloxy such as phenoxy and nitrophenoxy or that of a 2-equivalent type coupler having, as a split-off group, an ester-linkage group such as acetoxy and benzoyloxy. Moreover, as compared with conventional couplers, having a relatively analogous structure, the couplers of this invention can easily be dispersed in a protective colloid such as a gelatin. Among the couplers of this invention, oil-soluble couplers have an excellent solubility in coupler solvents, and couplers having a hydrophilic group exhibit excellent characteristics in Fischer dispersion. The couplers of this invention can easily be added to a liquid developer (these couplers are called external couplers, herein after). By virtue of these excellent characteristics, especially when the couplers of this invention are incorporated into photosensitive layers of photographic photosensitive materials, the thickness of the photosensitive layer can be greatly reduced, the sharpness and other properties of the resulting dye images can be improved, and there is no adverse interaction in color development (these couplers are called internal couplers hereinafter). Still further, by virtue of good reactivity, color contamination and the like can be highly improved with use of the couplers of this invention.

As previously mentioned, dyes obtained by employing the couplers of this invention have excellent color absorption characteristics.

Apparent from the foregoing description, the couplers of this invention have various applicabilities and they are used for attaining various objects by choosing a suitable combination of a coupler body and a split-off group. For example, couplers, having a water-soluble group, such as sulfonyl and carboxyl in the cyan coupler residue have good dispersibility. Couplers in which the bonding group-containing split-off group per se has dispersibility can be used as diffusible couplers. These couplers are utilized in the so called external photography coupler-in-developer type and can be incorporated into, for example, a color-forming liquid developer. For instance, coupler (22) can be mentioned as a coupler of this type.

Couplers of this invention in which the cyan coupler residue has dispersibility, the split-off group has appropriate non-dispersibility because it has a non-dispersible group such as an aliphatic long-chain hydrocarbon residue, e.g., octadecyl. However, the entire structure consisting of the cyan coupler residue and split-off group has dispersibility and can be utilized in external photography as well as the above-mentioned type couplers.

Couplers (16), (17), (18), (19), (20) and (21) can be mentioned as preferred couplers for the external photography in addition to the above-mentioned coupler (22).

As is well known in the art of external photography, a coupler is incorporated into a color-forming liquid developer, and a coupler-free photosensitive material, especially a silver halide photosensitive material for black-white photography (prepared for external photography), is exposed to light and developed with the coupler-containing color-forming liquid developer. On the development, both the color-forming developing agent and coupler intrude into the photosensitive material and the color-forming developing agent reacts with the diffusible coupler in the presence of a silver halide having a development center. This results in the formation of a dye image. In order to obtain a multicolor image, the development is generally carried out by employing successive color-forming liquid developers containing different couplers (for example, a cyan coupler, a magenta coupler and a yellow coupler).

Such color-forming liquid developer can comprise, in addition to the color-forming developing agent and coupler, various photographic additives used in ordinary color-forming liquid developers, such as sulfites, carbonates, bisulfites, bromides and iodides of alkali metals, and the like. A typical example of the composition of such a liquid developer is as follows:

| Composition of Color-Forming Liquid Developer: | |
|---|---|
| Color-forming developing agent | 1 – 5 g |
| Anhydrous sodium sulfite | 1 – 3 g |
| Anhydrous sodium carbonate | 10 – 60 g |
| Potassium bromide | 0.5 – 1.5 g |
| Coupler | 1 – 3 g |
| Water | balance |
| Total | 1 liter |

An external color-forming liquid developer containing a coupler of this invention, especially one suitable for the external photography such as mentioned above, has good solubility as compared with liquid developers comprising conventional couplers and exhibits excellent properties such as these mentioned above.

Couplers in which the cyan coupler residue is diffusible, the split-off group is diffusible but the entire coupler structure is non-diffusible; couplers in which the cyan coupler residue is non-diffusible, the split-off group is diffusible but the entire coupler structure is non-diffusible; and couplers in which the cyan coupler residue is non-diffusible, the split-off group is diffusible and the entire coupler structure is diffusible; are suitable for use in the diffusion transfer type photographic process. Imparting diffusibility to each group can be accomplished by selecting a low-molecular weight group and/or introducing a water-soluble hydroxyl group such as sulfenyl and the like. Imparting non-dispersibility to each group can be accomplished by introducing a long-chain aliphatic hydrocarbon residue and/or selecting a relatively high-molecular-weight group.

As a specific example of the coupler to be used for the diffusion transfer type photography, there can be mentioned couplers in which chemical-seeds are unnecessary for image formation at color-forming development though either the cyan coupler residue or the split-off group is diffusible. For example, couplers formed by introducing a hydroquinone residue, a resorcin residue or the like into either of the cyan coupler residue and split-off group, with or without an appropriate bonding group, can be effectively used for the diffusion transfer type photography. This means can be applied to other type couplers differing in the combination of dispersibility and non-dispersibility between the cyan coupler residue and split-off group. When the diffusion transfer type photographic process is adopted, the image forming method is divided into two types; one utilizing a cyan dye obtained by the reaction between the cyan coupler residue and the color-forming developing agent, and the other utilizing the split-off group portion sprit off in color development. In the former method, it is necessary that the obtained cyan dye is diffusible, and in the latter method, it is indispensable that the compound formed by isolation of the split-off group from the active position is diffusible. When such an isolated compound is utilized, it is necessary that said compound should be colored. In short, such compound includes a dye content such as an azo dye. Examples of the split-off group of this type are represented by the following general formula (VII):

Formula [VII]

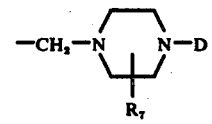

wherein $R_7$ is a monovalent organic residue which can be D, and D stands for a dye residue.

In the general formula (VII), the dye residue D has, preferably, a water-soluble group and it is preferred that the dye residue D is a monovalent residue of a dye selected from azo dyes, azomethine dyes, indoaniline dyes, indophenol dyes and anthroquinone dyes.

As the coupler suitable for the diffusion transfer type photographic process, there can be mentioned, for example, couplers (4), (10), (14) and (15).

As is well known in the art, a combination of a photosensitive material and an image-receiving material is employed in the diffusion transfer type photography, and according to this photographic method, after exposure of the photosensitive material, it is superposed on the image-receiving material at least during the development step to form an image on the image-receiving material. For instance, a coupler-containing a silver halide photosensitive material is used in combination with an image-receiving material comprising an image-receiving layer formed on a support through an undercoating layer, an intermediate layer and the like. After exposure of the silver halide photosensitive material, the photosensitive layer of the photosensitive material is superimposed on the image-receiving layer of the image-receiving material, if desired, through a protective layer, and a color-forming liquid developer is inserted into the clearance between the two layers to effect development. Thus, the dye formed on the photosensitive layer is transferred onto the image-receiving layer by diffusion, and, finally, the image-receiving material is peeled off from the photosensitive material whereby a dye image is formed on the image-receiving material. Various methods of diffusion transfer type photographic processes are known. For instance, there can be mentioned a method in which the photosensitive material is integrated with the image-receiving material and the steps of superimposing the image-receiving material on the photosensitive material and peeling off the image-receiving material from the photosensitive material are omitted. In this method, if a boundary layer between the image-receiving material and photosensitive material or a layer adjacent thereto is an opaque layer, a support for the photosensitive material is transparent and light exposure is effected from the side of the support of the photosensitive material. If a boundary layer or a layer adjacent thereto is substantially transparent, in order for the resulting image not to be influenced by the image formed in the photosensitive material, at least one of the above layers should be specified at the step conducted after the light exposure, for instance, at the color-forming development step. In this combination of the image-receiving material and photosensitive material, at least a support on the side of the image-receiving material should be transparent and the light exposure is effected from the side of the image-receiving material. After the light exposure, a color-forming liquid developer is injected into the boundary between the photosensitive material and image-receiving material or in the vicinity thereof, and an image is formed on the image-receiving layer.

In another diffusion transfer type photographic method, a color-forming liquid developer is retained in advance in an image-receiving material, and the development and transfer treatments are performed only by superimposing such image-receiving material on a photosensitive material.

Couplers of this invention can be applied effectively to any of known diffusion transfer photographic methods. In general, the coupler is incorporated in a photosensitive material and use of a silver halide photosensitive material is preferred. The coupler is generally used in an amount of about 0.07 to about 0.7 mole, preferably 0.1 to 0.4 mole, per mole of the silver halide.

A coupler known as the so called internal coupler is used in the state incorporated in a photosensitive material, especially a silver halide photosensitive material. In order not to influence other layers, it is preferred that the employed coupler is non-diffusible. Among couplers used for the above-mentioned diffusion transfer photography, those that are non-diffusible can also be used effectively. It is preferred that a coupler in which the cyan coupler residue is non-diffusible and the split-off group is either diffusible or non-diffusible is used as the internal coupler.

Preferred instances of the coupler of this type are such as couplers (1), (2), (3), (4), (5), (6), (7), (8), (9), (10), (11), (12), (13), (14), and (15).

Some internal couplers are substantially colorless and are ordinary couplers capable of forming a dye by the reaction with an oxidation product of the color-forming developing agent formed at the development step. Other internal couplers are colored couplers and are preferably used for color correction in the so called masking process. For color correction in the masking process, couplers (3) and (10) are preferably employed. In color correction in the masking process, the color of the colored coupler per se is decolorized or is excluded from the system of the photosensitive material at color-forming development, and, simultaneously, a cyan dye is formed by its reaction with a color-forming developing agent. In general, a colored coupler of this type is used in combination with a substantially colorless coupler.

Internal couplers are divided into two types depending on whether they contain, in the molecule, a hydrophilic group or an oleophilic group. Namely, they are divided into the Fischer dispersion type which is incorporated in the form of an alkaline liquid into a coating composition for formation of a photosensitive layer and the protect type which is incorporated in the state dissolved in a coupler solvent. As the former type, there can be typically mentioned couplers (12) and (13). When the couplers of this invention are dispersed by appropriate means depending on the above-mentioned types, they exhibit a much higher solubility than conventional couplers, and, hence, they provide such advantages as formation of a higher density image, improvement of the layer transparency and the resolving power.

If the coupler of this invention is incorporated into a photosensitive material, it is generally used in an amount of about 0.07 to about 0.7 mole, preferably 0.1 to 0.4 mole, per mole of a silver halide. If the coupler of this invention is used for color correction in the masking process or it is used for improving characteristics of other coupler or for other purposes, the coupler is generally used in an amount of about 0.01 to about 0.1 mole, preferably about 0.03 to about 0.07 mole, per mole of a silver halide.

As described hereinabove, couplers of this invention can be applied in various ways depending on the intended purpose, and they exhibit excellent characteritics in each application.

A preferred photosensitive material to which the coupler of this invention is applied is a silver halide photosensitive material, and the coupler of this invention can be used for various silver halide photosensitive materials. For example, the coupler of this invention can be used for silver halide photosensitive materials for the above-mentioned diffusion transfer type photography, ordinary negative photosensitive materials, ordinary reversal photosensitive materials, ordinary positive photosensitive materials, direct positive photosensitive materials, special photosensitive materials (such as photosensitive materials for printing, X-ray photosensitive materials, high resolving power photosensitive materials, infrared photosensitive materials and ultraviolet photosensitive materials), and other silver halide photosensitive materials.

As the silver halide to be used for such photosensitive materials, there can be mentioned, for example, silver chloride, silver iodide, silver iodobromide, silver chlorobromide, silver chloroiodobromide, etc. These silver halides are prepared according to various methods such as the neutral method, the ammonia method, the simultaneously mixing method and conversion method, and a suitable method is chosen depending on the intended type of the photosensitive material. If a mixed silver halide, is used the mixing ratio of two or more of silver halides is appropriately chosen. For example, a silver halide having a relatively low sensitivity and a relatively fine particle size is composed mainly of silver chloride, and the content of silver chloride is reduced in a mixed silver halide having a relatively high sensitivity. As the silver halide used for a direct positive photosensitive material, there can be mentioned, for example, Herschel reversal type silver halides and solarization type silver halides. In general, appropriate chemical or optical fogs are imparted in advance to these silver halides. Further, these silver halides are chemically sensitized by active gelatin; sulfur sensitizers such as allylthiocarbamide, thiourea and cysteine selenium sensitizers; reducing sensitizers such as stannous salts and polyamines; and noble metal sensitizers such as gold sensitizers, e.g., potassium aurithiocyanate, cerium chloroaurate and 2-aurosulfobenzothiazole methochloride, and sensitizing amounts of water-soluble salts of ruthenium, rhodium, iridium and the like, e.g., ammonium chloropalladate, potassium chloroplatinate and sodium chloropalladide (some of these sensitizers act as a sensitizer of a fog inhibitor depending on the amount used). These sensitizers can be used alone or in combination of two or more. For example, a combinaton of a gold sensitizer and a sulfur sensitizer and a combination of a gold sensitizer and a selenium sensitizer are used for the chemical sensitization.

Silver halides can be optically sensitized in a desired wave-length region. For example, they can be optically sensitized (for example, hypersensitized) by one or more of cyanine dyes such as zeromethine dyes, monomethine dyes, dimethine dyes and trimethine dyes, merocyanine dyes, and other optical sensitizers.

Such silver halide is dispersed in a suitable protective colloid to form a photosensitive layer. As the protective colloid to be used for formation of a photosensitive layer and other structural layers such as an intermediate layer, a protective layer, a filter layer, an image-receiving layer and a pH-adjusting layer (for example, an undercoat of the image-receiving layer), gelatine is generally employed, and in addition, there are employed colloidal albumin, cellulose derivatives, polyvinyl compounds (for example, polyvinyl alcohol) and other synthetic resins. They can be used alone or in the form of a mixture of two or more. Further, it is possible to employ acetyl cellulose having an acetyl content of about 19 to about 26% or water-soluble ethanolamine cellulose acetate in combination with the foregoing protective colloids.

As the support of a photosensitive material, there can be employed paper, laminated paper (for example, a laminate of polyethylene and paper), glass, and a film or sheet of such a substrate as cellulose acetate, cellulese nitrate, polyester, polycarbonate, polyamide, polystyrene and polyolefin. In order to improve the adhesive property of such support to each structural layer, the support can be subjected to various surface treatments for rendering it hydrophilic. For example, the support can be subjected to the saponification treatment, corona discharge treatment, undercoat treatment, setting treatment and the like.

A photosensitive material comprises at least a support and a photosensitive layer formed thereon. In general, a photosensitive material has a multilayer structure composed of at least several layers in which suitable layers are so disposed at various positions as to attain objects such as mentioned above. For example, a photosensitive material for color photography can include at least two photosensitive layers sensitized in different wavelength regions and each photosensitive layer can contain a coupler to form a color different from the color of the coupler contained in the other photosensitive layer.

Since a cyan coupler residue portion is utilized in the coupler of this invention, a cyan dye is formed, and the cyan coupler of this invention is used for a photosensitive material for color photography in combination with other 2-equivalent and 4-equivalent type couplers such as magneta couplers, e.g., 5-pyrazolones, and yellow couplers having an active methylene group inserted between two carbonyl groups. In a pseudo-color photosensitive material, the coupler of this invention can be used alone or in combination with a similar cyan coupler, and the relation between the sensitive wavelength region and the color of dyes derived from the coupler are not always in accord with such relation as found in an ordinary color photosensitive material.

A photosensitive layer sensitive to a certain wavelength region may comprise two or more layers differing in the sensitivity, and couplers forming the same color but a different type, for example, a combination of 2-equivalent type and 4-equivalent type couplers, can be incorporated into respective layers. Such multilayer photosensitive material is adopted for further improving the resolving power or attaining other objects.

As indicated above, the coupler of this invention can be combined with other 2-equivalent type or 4-equivalent type couplers. For example, so called colored couplers (having a split-off group including as a bonding group an azo group at the active point), so called D. I. R. couplers (releasing a development inhibitor at the development step) and the like can be combined as the 2-equivalent type coupler.

A photographic photosensitive material can additionally contain various photographic additives in the photosensitive layer and/or other structural layers (such as intermediate, undercoat, filter, protective and image-receiving layers), and as such photosensitive additives, there can be employed, for example, stabilizers such as mercury compounds, triazoles, azaindenes, zinc salts and cadmium salts; sensitizers such as quaternary ammonium salts and polyethylene glycol; film property-improving agents such as glycerin, dihydroxalkanes, esters, ethylene-bis-glycolic acid and emulsions or dispersions of polymers; film-hardening agents such as formaldehyde, halogen-substituted fatty acids, disulfonyl chloride, bisaziridine and ethyleneimines; extenders such as saponin, lauryl and oleyl monoethers of polyethylene glycol and sulfated and alkylated polyethylene glycol salts; organic solvents such as coupler solvents (high-boiling-point organic solvents and/or low-boiling point organic solvents, for example, dibutyl phthalate, tricresyl phosphate, acetone, methanol, ethanol and ethylene cellosolve); so called D. I. R. compounds capable of releasing a development inhibitor and forming a substantially colorless compound at the development step; antistatic agents; defoaming agents; ultraviolet absorbers; fluorescent whitening agents; stop-preventive agents, matting agents; halation-preventive agents and irradiation-preventive agents. These photographic additives can be used alone or in combination.

An image-receiving material which is an individual layer independent from a photosensitive material and is used for the diffusion transfer type photography in combination with a photosensitive material comprises at least an image-receiving layer formed on such a support as mentioned above. It may further comprise a protective layer, an undercoating layer, a pH-adjusting layer and the like according to need. Each layer comprises a protective colloid such as mentioned above as a layer-forming material, and various photographic additives such as mentioned above can be incorporated therein according to need. For example, in order to prevent rediffusion of a diffusible dye diffused from the photosensitive layer or color bleeding at the color development of the image-receiving layer, it is desired that a compound having a capability of catching a dye or a compound having an ability to annul the dispersibility of a dye is incorporated into the image receiving layer. It is also possible to incorporate such compound into a layer adjacent to the image-receiving layer. Typical instances of such compound are mordants such as polymers of an aminoguanidine derivative of vinylmethylketone disclosed in U.S. Pat. No. 2,882,156 and mordants disclosed in U.S. Pat. Nos. 3,271,148 and 3,271,147 and pH-adjusting agents such as inorganic and organic acids.

As indicated above, a color-forming liquid developer for color formation and development of an exposed photosensitive material comprises a developing agent as a main ingredient. As the developing agent, there are typically employed p-phenylenediamines such as diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)-toluene, N-ethyl-N-$\beta$-methanesulfonamidoethyl-3-methyl-4-aminoaniline sulfate, N-ethyl-N-$\beta$-methanesulfonamidoethyl-4-aminoaniline, 4-N-ethyl-N-$\beta$-hydroxy-ethylaminoaniline and the like.

These developing agents can be used alone, or mixtures of two or more may be used. These developing agents can be used, if desired, in combination with developing agents for black-white photography, such as hydroquinone and the like. Further, these developing agents for color photography can contain alkalis such as sodium hydroxide, ammonium hydroxide, sodium carbonate, sodium sulfate and sodium sulfite and other various additives such as alkali metal halides, e.g., potassium bromide and development-adjusting agent, e.g., citrazinic acid. In some diffusion transfer type photographic methods, this developing agent for color photography is incorporated in advance into an image-receiving material. In such methods, the color-framing developing agent is separated from the alkali, and only one of the developing agent and alkali is incorporated into the image-receiving layer. This layer is treated with a liquid containing the other component at the development step.

The coupler of this invention reacts with an oxidation product of the color-forming developing agent formed on development of a silver halide with such color-forming liquid developer to form a cyan dye, and some couplers provide other dyes (inclusive of cyan dyes).

In case the silver halide contained in the photosensitive material or developed silver is removed outside the system after such color-forming development treatment, a fixing liquid, a bleaching liquid, a combination of a fixing liquid and a bleaching liquid, a bleaching-fixing liquid and the like are employed. Treatments with these liquids are conducted in combination with other treatments such as water-washing treatment, stopping treatment, stabilizing liquid treatment and the like. As the fixing component, there can be employed, for example, solvents for silver halides such as sodium thiosulfate and ammonium thiosulfate, and as the bleaching component, there can be employed, for example, red prussiate, and ammonium, ferric and sodium salts of ethylenediamine tetraacetic acid.

The coupler of this invention is superior to conventional 2-equivalent type couplers in various photographic characteristics.

This invention will now be described in more detail by reference to the following Examples which do not limit the scope of this invention. In the examples, the following couplers are used as comparative couplers.

Comparative coupler 1 (disclosed in U.S. Pat. No. 2,474,293)

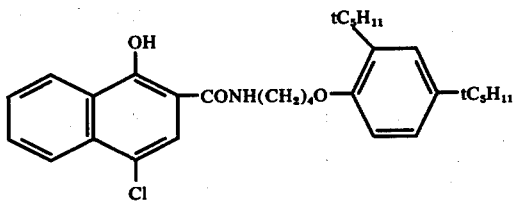

Comparative coupler 2 (disclosed in U.S. Pat. No. 3,034,892)

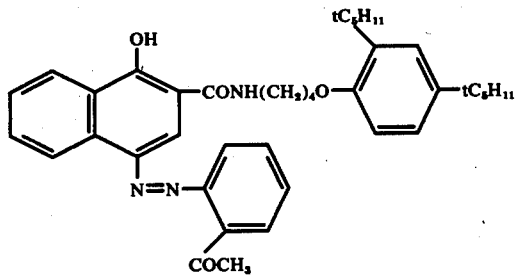

EXAMPLE 1

10 g of a coupler as indicated in Table 1 given below was added to a liquid mixture of 20 ml of dibutyl phthalate and 60 ml of ethyl acetate. The mixture was heated at 60° C. to completely dissolve the coupler. The resulting solution was mixed with 5 ml of a 10% aqueous solution of Alkanol B (alkylnaphthalene sulfonate manufactured by Du Pont) and 200 ml of a 5% aqueous solution of gelatin, and the mixture was emulsified by means of a colloid mill to form a coupler dispersion.

The so formed dispersion was added to 500 g of a gelatin emulsion for negative including silver iodobromide (containing 6.0 mole % of silver iodide), and the mixture was coated and dried on a cellulose triacetate film base.

The so obtained sample was exposed to light and developed at 20° C. for 10 minutes with a color-forming liquid developer having the following composition:

| | |
|---|---|
| N-ethyl-N-$\beta$-methanesulfonamidoethyl-3-methyl-4-aminoaniline sulfate | 5.0 g |
| Anhydrous sodium sulfite | 2.0 g |
| Sodium carbonate (monohydrate) | 50.0 g |
| Potassium bromide | 1.0 g |
| Sodium hydroxide | 0.55 g |
| Benzyl alcohol | 4.0 ml |
| Water | balance |
| Total | 1 liter |

The so treated sample was subjected to customary stopping and fixing treatments and washed with water for 10 minutes. Then, the sample was bleached at 20° C. for 5 minutes with a bleaching liquid having the following composition:

| | |
|---|---|
| Red prussiate | 100 g |
| Potassium bromide | 50 g |
| Water | balance |
| Total | 1 liter |

Then, the sample was washed with water for 5 minutes, and subjected to the fixing treatment at 20° C. for 5 minutes by employing a fixing liquid having the following composition:

| | |
|---|---|
| Sodium thiosulfate (pentahydrate) | 250 g |
| Water | balance |
| Total | 1 liter |

The sample was washed with water for 25 minutes and then dried.

The so treated sample was tested with respect to photographic characteristics to obtain results shown in Table 1.

Table 1

| Sample No. | Coupler Used | Relative Sensitivity | γ-Value | Maximum Density (Dmax) | Absorption Maximum Wavelength (max) | Image Photo-resistance | Moisture Resistance |
|---|---|---|---|---|---|---|---|
| 1 | coupler (1) | 127 | 1.75 | 2.32 | 700 nm | 91 % | 75 % |
| 2 | coupler (3) | 110 | 1.71 | 2.13 | 700 nm | 90 % | 72 % |
| 3 | comparative coupler (1) | 100 | 1.53 | 2.00 | 700 nm | 87 % | 70 % |

In the above Table, the value of the sensitivity is a relative value calculated based on the sensitivity (100) of the sample 3 using comparative coupler (1).

The photo-resistance of each sample was determined by subjecting each resulting image to exposure for 16 hours by employing an xenon fadometer and expressing the residual density in terms of the percentage based on the density (100) before the exposure. The moisture resistance was determined by storing the resulting image under a condition of a relative humidity of 80% for 2 weeks and expressing the residual density in terms of the percentage based on the density (100) before the storage test.

As is apparent from the results shown in Table 1, the coupler of this invention shows excellent photographic characteristics (high sensitivity, excellent photo-resistance, excellent moisture resistance and the like), and a sample using the coupler of this invention provides a dye image having a high sharpness.

When the above procedures were repeated by employing couplers (6), (7), (9) and (11) instead of couplers (1) and (3), it was found that each of them had similar excellent photographic characteristics as the internal coupler.

EXAMPLE (2)

10 g of coupler (5) was added to a mixture of 20 ml of tricresyl phosphate and 60 ml of ethyl acetate and the mixture was heated at 60° C. to dissolve the coupler completely. The resulting solution was incorporated into 200 ml of a 5% aqueous solution of gelatin together with 5 ml of a 10% aqueous solution of Alkanol B. This was emulsified by means of a colloid mill to form a coupler dispersion.

The resulting dispersion was added to 500 g of a red-sensitive, highly sensitized emulsion of silver iodobromide (containing 4.0 mole % of silver iodide), and the mixture was coated and dried on a cellulose acetate film base to obtain a photosensitive material having a stable coating.

In the same manner as described in Example 1, this photosensitive material was exposed to light and developed at 21° C. for 12 minutes with a liquid developer having the following composition:

| | |
|---|---|
| Metol | 3.0 g |
| Anhydrous sodium sulfite | 50.0 g |
| Hydroquinone | 6.0 g |
| Anhydrous sodium carbonate | 40.0 g |
| Potassium bromide | 3.5 g |
| Potassium thiocyanide | 2.0 g |
| Water | balance |
| Total | 1 liter |

The developed sample was subjected to customary stopping, film-hardening and water-washing treatments and it was then subjected to secondary exposure to white light.

Then, the sample was subjected to color-forming development at 21° C. for 13 minutes by employing a color-forming liquid developer having the following composition:

| | |
|---|---|
| N,N-diethyl-2-methyl-p-phenylenediamine | 3.0 g |
| Anhydrous sodium sulfite | 4.0 g |
| Sodium carbonate (monohydrate) | 20.0 g |
| Potassium bromide | 2.0 g |
| Water | balance |
| Total | 1 liter |

The sample was subjected to stopping, water-meshing, bleaching and fixing according to customary methods, washed for 20 minutes with running water and dried to obtain a positive colored image of a cyan dye having an absorption maximum at 700 nm and being excellent in transparency.

From the results shown in Table 2, it will readily be understood that the coupler of this invention indicates excellent photographic characteristics also in a reversal photosensitive material.

When the above example was repeated using coupler 9 in place of coupler 5, excellent results similar to the above were obtained.

EXAMPLE (3)

2.0 g of a coupler as shown in Table 2 at forth later was dissolved in 2.0 ml of tricresyl phosphate and 6.0 ml of ethyl acetate and a coupler-emulsified dispersion was prepared in the same manner as in Example 1. The resulting dispersion was added to 100 ml of a highly sensitized silver iodobromide emulsion and the mixture was coated and dried on a film base to obtain a photosensitive material.

The so obtained photosensitive material was exposed to light according to a customary method and developed at 38° C for 3 minutes and 15 seconds with a color-forming liquid developer having the following composition:

| | |
|---|---|
| N-ethyl-N-(β-hydroxyethyl)-3-methyl-4-aminoaniline hydrochloride | 5.0 g |
| Anhydrous sodium sulfite | 2.0 g |
| Sodium carbonate | 50.0 g |
| Potassium bromide | 1.0 g |
| Sodium hydroxide | 0.55 g |
| Water | balance |
| Total | 1 liter |

Then the sample was bleached at 38° C. for 6 minutes with a bleaching liquid having the following composition:

| | |
|---|---|
| Disodium ethylenediamino tetraacetate | 40.0 g |
| Ferric chloride | 30.0 g |
| Sodium carbonate (monohydrate) | 20.0 g |
| Potassium bromide | 30.0 g |
| Water | balance |
| Total | 1 liter |

Then, the sample was water-washed fixed and stabilized according to customary methods so that cyan dye images, having a maximum absorption of 700 nm, in addition to positive images having a maximum absorption around 500 nm were obtained which show excellent color characteristics. The samples were further tested and determined to achieve the results shown in Table 2.

The so obtained sample was light-exposed and treated at 24° C. for 3 minutes with an alkaline liquid developer having the following composition:

| | |
|---|---|
| Sodium sulfite | 2.0 g |
| 4-N-ethyl-N-β-hydroxyethyl aminoaniline | 11.0 g |
| Water | balance |
| Total | 1 liter |

During the above development treatment, the photosensitive layer of the above sample was closely contacted with an image receiving layer comprising dimethyl-β-hydroxyethyl-γ-stears amido propyl ammonium-hydrogen phosphate, the layer being coated on a polyethylene laminated paper. After the development, the image receiving layer was pealed off from the photosensitive layer, so that clear cyan positive images, having excellent photographic characteristics, were obtained in the image receiving material. The coupler of this invention proved excellent in diffision-transfer photography.

EXAMPLE 5

Coupler 16 was dissolved in methanol and the resulting solution was added to the following liquid developer for external development:

| | |
|---|---|
| N,N-di-ethyl-2-methyl-p-phenylenediamine | 2.0 g |
| Anhydrous sodium sulfite | 2.0 g |
| Sodium carbonate (monohydrate) | 20.0 g |
| Potassium bromide | 1.0 g |
| Coupler 16 | 2.0 g |
| Water | balance |
| Total | 1 liter |

A photosensitive material, obtained by a highly sensitive silveriodobromide emulsion, was coated on an Table 2

| Sample No. | Coupler Used | Maximum density (Dmax) | Maximum absorption (λ max) | Maximum absorption of masking images (λ mask) | |
|---|---|---|---|---|---|
| 4 | coupler 4 | 135 | 1.87 | 700 nm | 550 nm |
| 5 | coupler 10 | 123 | 1.74 | 700 nm | 550 nm |
| 6 | comparative coupler 2 | 100 | 1.62 | 700 nm | 500 nm |

In the above table, the maxmum absorption of masking images is of couplers per se.

In the above example, the coupler of this invention was used as a coupler for color composition by a masking method. From the results shown in Table 2, the coupler of this invention has excellent photographic characteristics including a greater increase in sensitivity, density etc in addition to the improvement of image resolution when compared with the comparative coupler.

EXAMPLE 4

Coupler (15) of this invention was incorporated into an ordinary highly sensitized emulsion for negative having silver iodobromide according to the Fisher dispersion method (the coupler was used in an amount of 0.2 mole per mole of the silver halide). The emulsion was coated and dried on a cellulose triacetate film base according to a customary method.

undercoated polyethyleneterephthalate film base, and was exposed to light and then developed by the above developer for 3 minutes at 24° C.

After the development, four minute washing, five minute bleaching, five minute washing, five minute fixing, thirty minute washing and drying were carried out in turn according to a customary method to obtain cyan dye images having excellent photographic characteristics including excellent color absorption characteristics with the maximum absorption of 700 nm.

The above example was repeated except that coupler 20 was employed in place of coupler 16 and excellent dye images having a maximum absorption of 680 nm were obtained. The couplers of this invention are very useful as couplers for external development.

EXAMPLE 6

Dispersion A:
Prepared by the same manner as Example 1 except using a solution that 0.15 g of coupler (4) and 2.0 g of 1-hydroxy-N-[δ-(2,4-di-t-amylphenoxy)butyl]-2-naphtoamide which is known, are dissolved in the mixture of 2.2 ml of tricresylphosphate and 6.0 ml of ethylacetate.

Dispersion B:

0.2 g of 2-(1-phenyl-5-tetrazolythio)-4-(α-2,4-di-t-amylphenoxy acetamido) indanone (a developing inhibitor releasing type compound) is added to dispersion A.

Dispersion C:

0.1 of 1-hydroxy-4-(1-phenyl-5-tetrazolythio)-2-(2-tetradecyloxyphenyl)naphthaamide (a developing inhibitor releasing type coupler) is added to dispersion A.

Dispersion D:

Same as the dispersion B except that the comparative coupler (2) is used instead of the coupler (4). These dispersions are individually added to 100 ml of a highly red-sensitive silver iodobromide emulsion (7.0 ml % AgI) and the resulting dispersions are coated on individual film supports and dried to thereby obtain four samples.

These samples are exposed to light in an ordinary manner and processed in the same manner as Example 3.

The results of the photographic test are shown in Table 3 in which RMS is 1000 times value of standard deviation of densities obtained by scanning the examples by a microdensitometer having a round aperture of 2.5 μ, and U 0.5 is the spatial frequency when the MT factor decreased to 50%.

Table 3

| Sample | Fog | Relative Sensitivity | γ-Value | Granurality (RMS) | Sharpness (U 0.5) |
|---|---|---|---|---|---|
| A | 0.21 | 100 | 1.00 | 55 | 51 |
| B | 0.12 | 96 | 0.80 | 41 | 40 |
| C | 0.14 | 93 | 0.78 | 43 | 42 |
| D | 0.15 | 90 | 0.75 | 46 | 43 |

As apparent from Table 3, sample B exhibits superior gradation. granularity and sharpness as compared to samples A, C and D.

What is claimed is:

1. A method for developing an imagewise exposed silver halide color photosensitive material which comprises conducting the development in the presence of at least one of p-phenylenediamines and a phenol or naphthol cyan coupler having, in the active position thereof, the following split-off group:

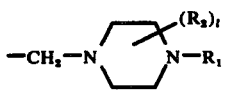

wherein $R_1$ is selected from the group consisting of alkyl, alkenyl, aryl, acyl, formyl, amino carbonyl group or a heterocyclic ring, said group and said ring may be substituted with a member selected from the group consisting of nitro; hydroxyl; amino; sulfo; substituted or unsubstituted alkyl, aryl, heterocyclic ring, alkoxy, arylazo, acylamino, or carbamoyl, said heterocyclic ring having 5 to 6 members and is selected from the group consisting of pyridyl, quinolyl, thienyl, piperidyl, imidazolyl and oxydiazolyl; $R_2$ is alkyl, alkenyl, aryl, acyl, formyl, or aminocarbonyl; and 1 is an integer of 0 to 4 inclusive.

2. The method according to claim 1 wherein the cyan coupler is represented by the following formula (I), (II), or (III):

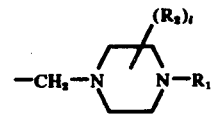

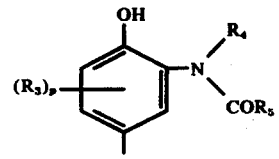

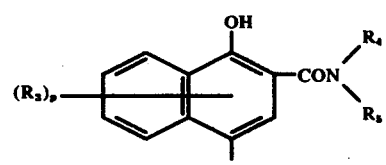

wherein $R_3$ is hydrogen, halogen, a substituted or unsubstituted aliphatic hydrocarbon, -O-$R_6$ or -S-$R_6$ in which $R_6$ is a substituted or unsubstituted aliphatic hydrocarbon; p is an integer of 1 to 3 inclusive provided that when p is greater than 1 each of more than two $R_3$'s in the same coupler can be different from the other; $R_4$ and $R_5$ are individually a substituted or unsubstituted group selected from an aliphatic hydrocarbon group, an aromatic hydrocarbon group and a heterocyclic ring, either of $R_4$ and $R_5$ can be hydrogen, and $R_4$ and $R_5$ can cooperatively form a heterocyclic ring containing nitrogen; and q is an integer of 1 to 5 inclusive.

3. The method according to claim 1 wherein $R_1$ and $R_2$ are individually aryl.

4. The method according to claim 1 wherein $R_1$ and $R_2$ are individually selected from the group consisting of alkyl and alkenyl.

5. The method according to claim 2 wherein $R_3$ is chlorine.

6. A silver halide color photosensitive material which comprises a support and a photosensitive layer thereon, said layer comprising silver halide grains and a phenal or naphthol cyan coupler having, in the active position thereof, the following split-off group

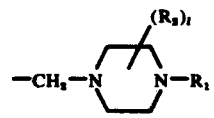

wherein R, is selected from the group consisting of alkyl, alkenyl, aryl, acyl, formyl, aminocarbonyl group or a heterocyclic ring, said group and said ring may be substituted with a member selected from the group consisting of nitro; hydroxyl; amino; sulfo; substituted alkyl, aryl, heterocyclic ring, alkoxy, arylazo, acylamino, or carbamoyl, said heterocyclic ring having 5 or 6 members and is selected from the group consisting of pyridyl, quinolyl, thienyl, piperidyl, imidazolyl, and oxydiazolyl; $R_2$ is alkyl, alkenyl, aryl, acyl, formyl, or aminocarbonyl; and 1 is an integer of 0 to 4 inclusive.

7. The photosensitive material according to claim 6 wherein said photosensitive material contains said coupler in an amount of 0.01 to 0.7 mole per mole of the silver halide.

* * * * *